(12) United States Patent
Shih

(10) Patent No.: US 8,932,366 B2
(45) Date of Patent: Jan. 13, 2015

(54) POROUS STRUCTURE AND A POROUS ASSEMBLY RESULTED THEREFROM FOR IMPLANTS

(75) Inventor: Grant Lu-Sun Shih, New Taipei (TW)

(73) Assignees: Grant Lu-Sun Shih, New Taipei (TW); Hung-Chou Yen, New Taipei (TW)

( * ) Notice: Subject to any disclaimer, the term of this patent is extended or adjusted under 35 U.S.C. 154(b) by 281 days.

(21) Appl. No.: 13/493,009

(22) Filed: Jun. 11, 2012

(65) Prior Publication Data

US 2013/0331893 A1    Dec. 12, 2013

(51) Int. Cl.
*A61F 2/28*    (2006.01)
(52) U.S. Cl.
USPC ...................................................... 623/23.57
(58) Field of Classification Search
CPC ....................................................... A61L 27/28
USPC ................................................. 623/23.5–23.6
See application file for complete search history.

(56) References Cited

U.S. PATENT DOCUMENTS

2013/0211540 A1*    8/2013    Tate et al. .................. 623/23.57

* cited by examiner

*Primary Examiner* — Sameh Boles
(74) *Attorney, Agent, or Firm* — Rosenberg, Klein & Lee

(57) ABSTRACT

A porous structure and a porous assembly resulted therefrom for implants allow a tissue to go through and attach for ingrowth, thereby achieving an ideal fixing effect. At least one porous structure is provided with a plurality of geometric-contoured apertures defined by walls. At least one channel is disposed on the apertures or the walls along a reference axis so that the adjoining apertures are intercommunicated, and the porous structures are connected and/or stacked with each other to contribute a porous assembly.

21 Claims, 6 Drawing Sheets

POROUS STRUCTURE AND A POROUS ASSEMBLY RESULTED THEREFROM FOR IMPLANTS

FIELD OF THE INVENTION

The present invention relates to a porous structure and a porous assembly resulted therefrom for implants, especially to a porous structure that allows a tissue to go through and attach for ingrowth; apertures of the porous structure are communicated with each other; when a plurality of porous structures are provided and connected to each other and/or stacked with each other, a porous assembly is further built.

DESCRIPTION OF THE RELATED ART

A fixing structure or an implant such as a screw or an artificial articulation is commonly applied in circumstances like dental caries, bon diseases, tumors, or traumas. Namely, the implant is embedded in an ill part or an inner part of a bone so as to rectify afore malformations. Thereby, the original appearance and correlated function can be resumed since the embedded implant helps heal and fix the broken bones or tissues. Accordingly, the implant is widely applied.

When the implant such as the screw or the artificial articulation for fixing is designed, the mechanics between the bone and the implant should be concurrently considered. Wherein, the higher strength is provided between the bone and the implant, the better fixing result or efficiency is contributed. Factors like the geometric property (formation) of the implant, the bone structure, or the bone integrity are involved. Accordingly, if the strength between the bone and the implant is insufficient, the implant such as the screw or the artificial articulation easily comes off and skews off. Apparently, such implant can not provide a preferable fixing effect.

As discussed before, the bone structure and the bone integrity also affect the fixing effect. Wherein, when the bone structure provides inferior integrity and the bone mass density is also low, a poor fixing result is caused by the implant. Further, the bone integrity may also fade away when the bone mass weakens in compliance with age. Accordingly, the osteoporosis easily occurs, and the bone healing delays. Namely, the loosening and skew implant usually exists in cases of osteoporosis.

A conventional means discloses an appearance of the implant is arranged with indentations or a rough surface. Wherein, when the implant is embedded, the tissue grows in the indentations or/and the rough surface in the post-rehabilitation of the rectification, so that a preferable attaching and fixing effect is provided.

A porous structure having a plurality of bonded sheets stacked with each other to form a network for distributing over a surface of an implant is disclosed in "Assembled Non-Random Foams" of a U.S. Pat. No. 7,208,222 B2. Wherein, each sheet has apertures that are arranged in a certain pattern. Each aperture does not communicate with the adjacent aperture. The sheets can be aligned or slightly staggered with each other, so that the sheets are jointly formed into the network. The apertures on an upper part of the sheet and the apertures on a lower part of the sheet are able to communicate with each other. Whereby, when the implant is embedded in an ill part, the bone tissue gives ingrowth along the apertures and attaches the network so as to achieve a preferable fixing effect.

As known by those skilled in the art, when the network is structured by the sheets, the adjacent apertures can not communicate with each other in a transverse axis, so that the bone tissue can only grows in the apertures along a longitudinal axis. Adversely, if the network is structured by the slightly staggered and stacked sheets, the growth of the bone tissue is even impeded. Therefore, the conventional means needs amendments.

In short, there are means disclosing various implants for fixing in bone surgery, and the implants are able to rectify malformations or fix bone structures after surgery. The inventor of the present invention considers the combination of the fixing means and the bone structure while designing a novel and inventive structure that is going to be distributed over the surface of the implant. Namely, the structure that is going to be distributed over the surface of the implant provides an ideal formation for the bone tissue to go through and attach for ingrowth, thereby achieving a favorable fixing effect. Moreover, chances of the slackened or skew screw are reduced to a minimum.

SUMMARY OF THE INVENTION

The main object of the present invention is to provide a porous structure and a porous assembly resulted therefrom for implants comprising at least one porous structure having a plurality of apertures and walls for defining the apertures; and at least one channel being parallel to or disposed on a reference axis, thereby allowing the adjoining apertures to be communicated with each other. Moreover, when a plurality of porous structures are connected and/or stacked with each other, the porous assembly is constructed, thereby assisting tissues in going through and attaching so as to contribute to a firm fixing effect.

Preferably, the apertures are formed into irregular geometric contours and/or arranged irregularly on the porous structure.

Preferably, the porous structure is arranged on a surface of a fixing structure such as the implant or a screw. The channel is disposed at a lower part of the wall, so that the adjoining apertures are able to communicate with each other.

Preferably, the porous structure is arranged or embedded on a base. Moreover, the base adopts a sheet, and the base can be distributed over the surface of the fixing structure such as the implant or the screw.

Accordingly, the adjoining apertures of the porous structure and the porous assembly resulted therefrom can be communicated with each other; namely, each of the apertures is intercommunicated. Thereby, when the implant is embedded in an ill part, a bone tissue goes through and attaches to every aperture and each channel, which allows the bone tissue and the porous structure and/or the porous assembly to form an integral. An ideal fixing effect is achieved.

Following embodiments along with drawings give the present invention more clear explanations.

DETAILED DESCRIPTION OF THE PREFERRED EMBODIMENTS

Figure 2:
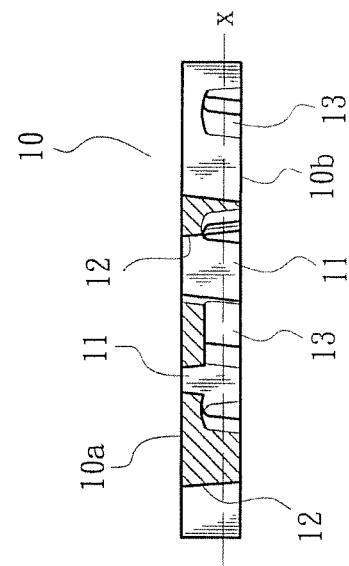
FIG. 2 is a cross-sectional view of FIG. 1.
Figure 1:
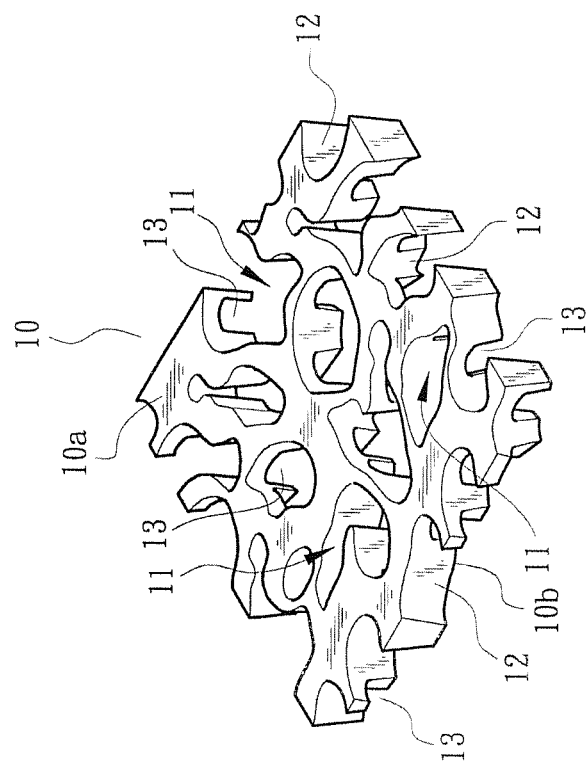
FIG. 1 is a schematic view showing an appearance of a porous structure of the present invention.

Referring to FIGS. 1 and 2, a porous structure and a porous assembly resulted therefrom for implants comprises at least one porous structure referred by the number 10 adopting a flexible material or a rigid material for being formed into a sheet with a geometric contour. In the figures, the porous structure 10 is formed into a square contour and includes a first surface 10*a* and a second surface 10*b*. In this embodiment, the first surface 10*a* and/or the second surface 10*b* are formed into a plane. A plurality of apertures 11 and walls 12 for defining the apertures 11 are arranged in the porous structure 10.

In FIG. 1, the apertures 11 on the first surface 10*a* are not communicated with each other. In FIG. 2, a first width of an upper part of the aperture 11 is smaller than a second width of a lower part of the aperture 11, and thereby the aperture 11 has a taper-shaped cross section.

In one embodiment, the apertures 11 are formed into regular and/or irregular geometric contours. Also, the apertures 11 are arranged on the porous structure in a regular pattern and/or in an irregular pattern. In the figure, the apertures 11 are arranged in an irregular pattern, so that a boundary of the porous structure 10 is provided with indentations.

In the preferred embodiment shown by FIGS. 1 and 2, at least one channel 13 is disposed on the apertures 11 or on the walls 12. Wherein, the channel 13 is parallel to or disposed on a horizontal reference axis $\chi$. Specifically, the channel 13 is disposed on the walls 12, or the channel 13 is disposed on a lower part of the wall 12 (or on the second surface 10*b*) so as to connect two adjoining apertures 11. Accordingly, the channel 13 allows the adjoining apertures 11 disposed on a lower part of the first surface 10*a* or on a part of the second surface 10*b* to intercommunicate. Imaginary lines in FIG. 3 explain the structure more clearly.

Figure 3:
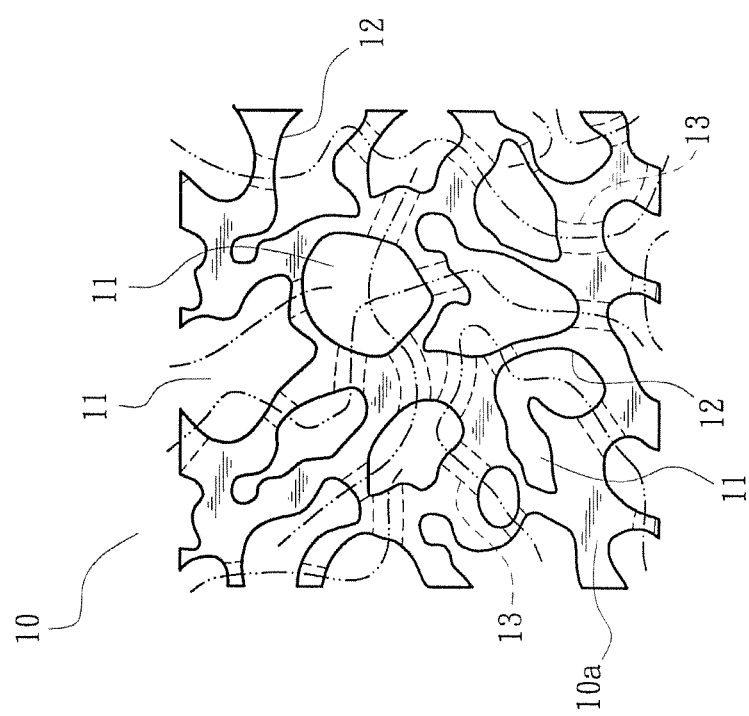
FIG. 3 is a schematic view of FIG. 1 showing that each aperture and every channel are intercommunicated by imagine lines.

FIG. 3 shows that the channel 13 not only allows the adjoining apertures 11 to intercommunicate but also allows all the apertures 11 on the porous structure 10 to intercommunicate. Whereby, when the porous structure 10 is distributed over or arranged on a surface of a fixing structure such as the implant or a screw, the porous structure 10 allows a bone tissue of an ill part to go through and attach to every aperture 11 and each channel 13 when the fixing structure is embedded in the ill part. Accordingly, the bone tissue and the porous structure 10 contribute to an integral, which achieves an ideal fixing effect.

Figure 4:
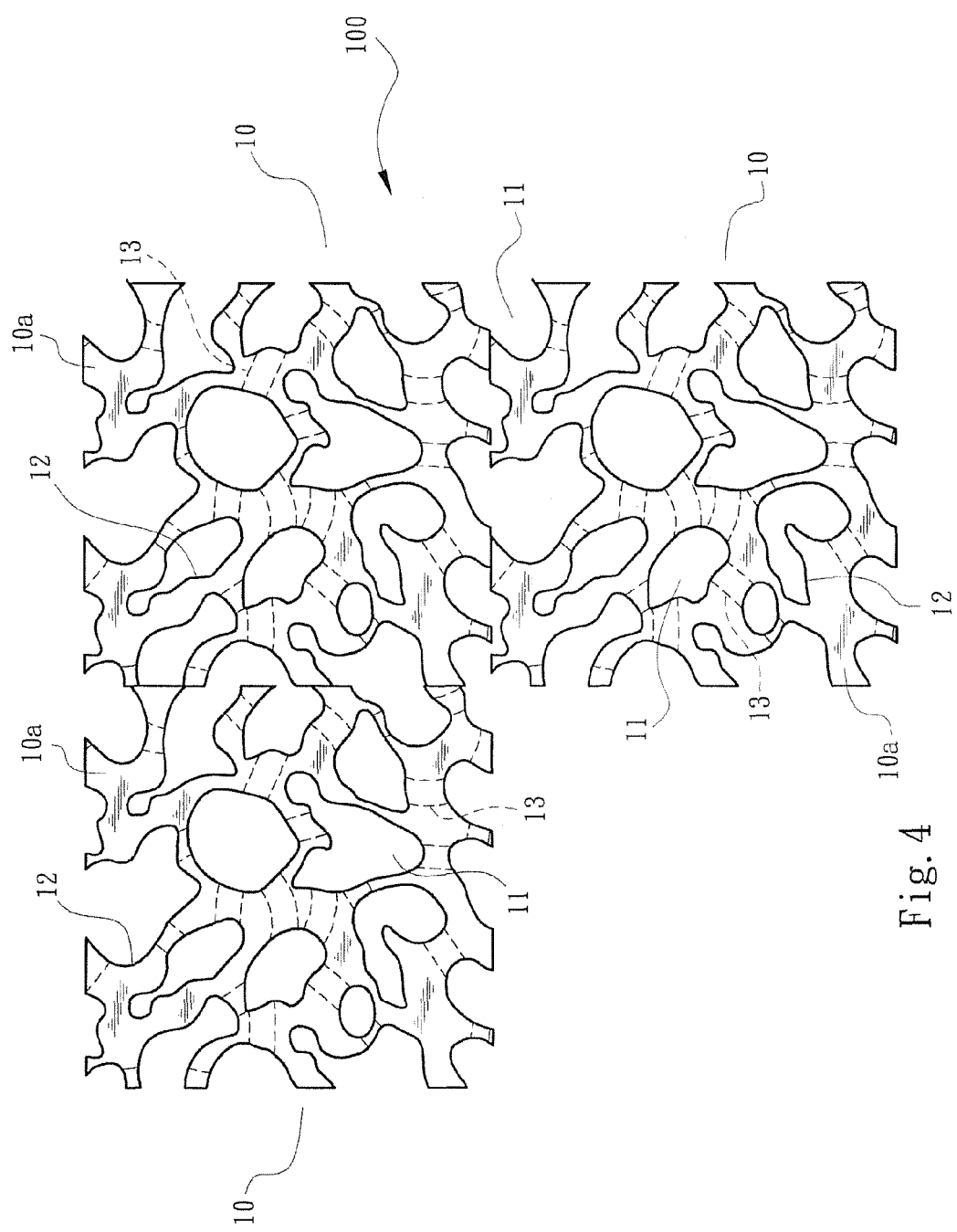
FIG. 4 is a schematic view showing a porous assembly resulted from the connective porous structures; the apertures and the channels of each porous structure of the porous assembly are intercommunicated.
Figure 5:
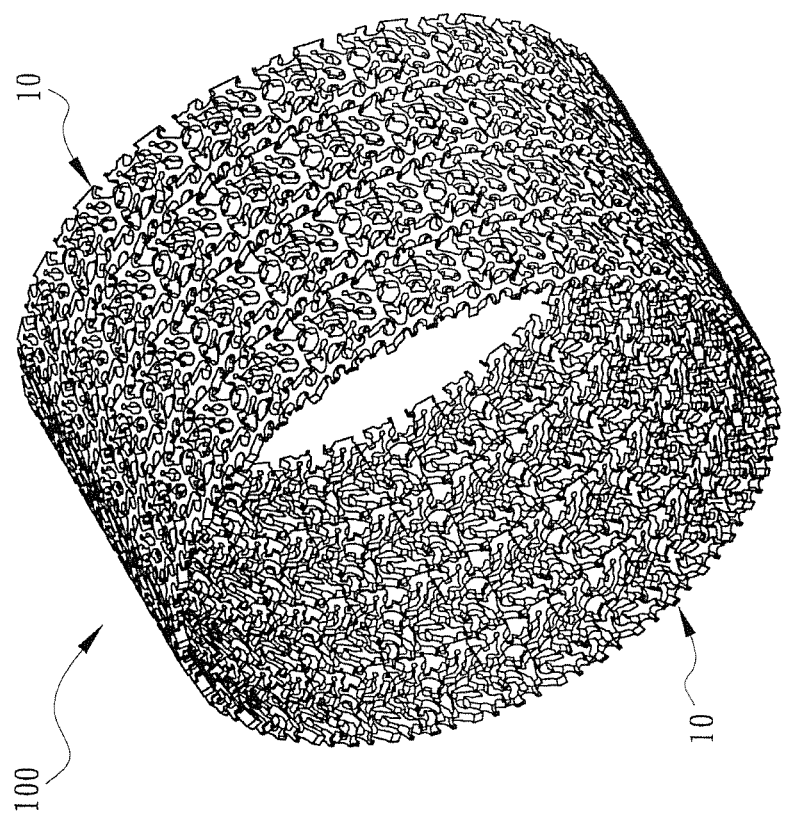
FIG. 5 is a schematic view of a preferred embodiment of the present invention that the porous structures are connected to form a porous assembly cylinder.

FIGS. 4 and 5 show a further preferred embodiment. A plurality of porous structures 10 are combined to construct a porous assembly 100. In FIG. 4, the apertures 11 and the channel 13 of the adjoining porous structures 10 allows every porous structure 10 or the porous assembly 100 constructed by the porous structures 10 to intercommunicate.

FIG. 5 shows the porous assembly 100 formed into a cylinder. In fact, the porous assembly 100 constructed by the porous structures 10 can be formed into other geometric formations such as a cone, a cuboid, a polyhedron, or etc. Specifically, the porous structures 10 can be connectively constructed and arranged on a designated object according to the practical formation of the object.

Figure 6:
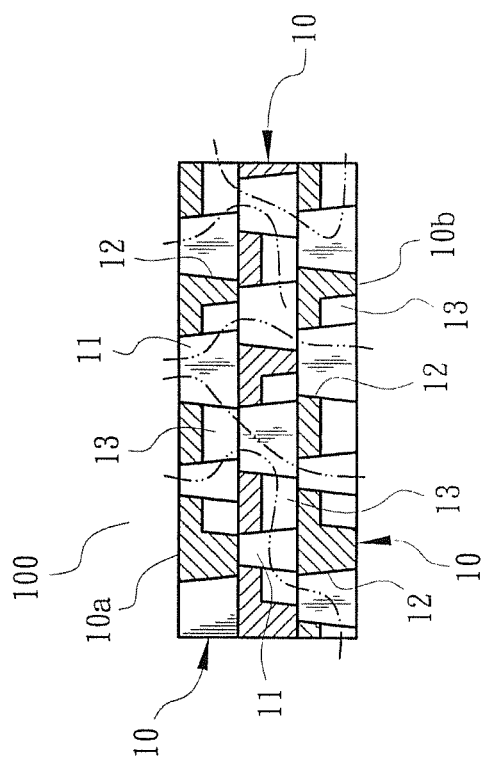
FIG. 6 is a schematic view showing that the porous structures are stacked with each other, and the imaginary lines depict that each aperture and every channel are intercommunicated.

FIG. 6 shows a similar preferred embodiment. A plurality of porous structures 10 are stacked to construct a porous assembly 100. In this figure, parts or all of the apertures 11 and the channels 13 are overlapped in the stacked porous structures 10, so that each porous structure 10 or the porous assembly 100 constructed by the porous structures 10 can intercommunicate.

Figure 8:
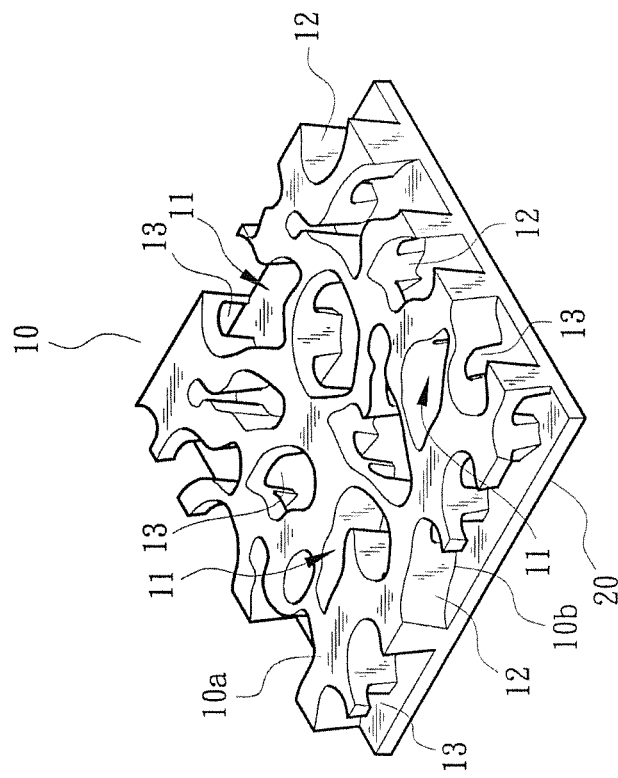
FIG. 8 is a schematic view showing a further preferred embodiment of the present invention; the porous structure is disposed on a base.
Figure 7:
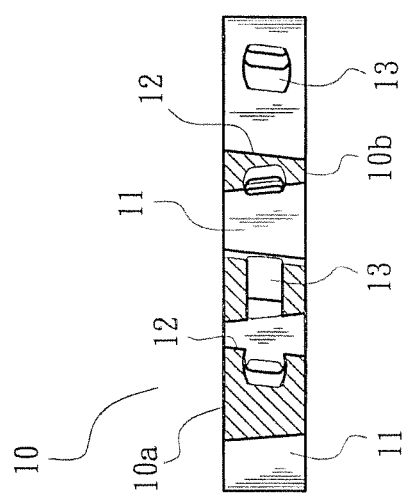
FIG. 7 is a schematic view of a further preferred embodiment of the present invention; the channel is disposed on a middle part of a wall for connecting the adjoining apertures.

FIG. 7 shows a further preferred embodiment for the porous structure 10. Herein, the channel 13 is disposed on a middle part of the wall 12 or between the first surface 10*a* and the second surface 10*b* so as to connect the adjoining apertures 11. FIG. 8 also shows a further preferred embodiment for the porous structure 10. Wherein, the porous structure 10 is disposed on or embedded in a base 20 that adopts a sheet. Moreover, the base 20 is distributed over or arranged on an object or the surface of the fixing structure such as the implant and the screw.

In a similar preferred embodiment, the base 20 is provided with a plurality of openings for communicating with the apertures 11 of the porous structure 10.

Preferably, the thicknesses of the first surface 10*a* and the second surface 10*b* are adjustable.

To sum up, the porous structure and the porous assembly resulted therefrom for implants are designed according to the following considerations:

1. The present structure of the invention is redesigned and benefits the ingrowth and the attachment of the bone tissue, which conduces to a favorable fixing effect. Accordingly, the fixing structure such as the screw does not retract or skew easily.

2. The structure of the present invention is different from that of the conventional one. Namely, the porous structure 10 of the present invention includes several apertures 11 and at least one channel 13 disposed on the apertures 11 or the walls 12, so that the adjoining apertures 11 can intercommunicate. Oppositely, in the conventional structure, the appearance of the implant is provided with indentations or a rough surface, so that pieces of sheets having openings arranged in a certain pattern are aligned or staggered with each other for stacking. Accordingly, the sheets of the conventional structure contribute to the network.

3. When the porous structures 10 are connected or stacked to form the porous assembly 100, the transversely and the longitudinally adjoining porous structures 10 are partially or integrally combined in view of the apertures 11 and the channel 13. Namely, each porous structure 10 or the porous assembly 100 constructed by the porous structures 10 can intercommunicate along a transverse axis or a longitudinal axis. Thereby, the arrangement of the present invention is more ideal for the bone tissue to go through and attach for ingrowth. In the conventional means, the transversely adjacent apertures in the network built by pieces of sheets can not intercommunicate. Accordingly, the bone issue can only grow along apertures in a longitudinal direction. Even worse, when the sheets are staggered, the growth of the bone tissue in the longitudinal direction is also affected. Preferably, the present invention prevents disadvantages existing in the conventional means.

Consequently, the structural arrangement of the present invention is different from that of the conventional means, thereby contributing to a novel configuration and inventive performances.

While we have shown and described the embodiment in accordance with the present invention, it should be clear to those skilled in the art that further embodiments may be made without departing from the scope of the present invention.

I claim:

1. A porous structure and a porous assembly resulted therefrom for implants comprising: at least one porous structure having a first surface and a second surface; a plurality of adjoining apertures and walls for defining said adjoining apertures being arranged in said porous structure; said adjoining apertures on said first surface being not communicate with each other; and at least one channel connecting to said adjoining apertures, so that at least parts of said adjoining apertures defined at a lower part of said first surface are able to communicate with each other, wherein a plurality of porous structures are connected with each other to build said porous assembly, wherein at least one aperture and/or said channel of each porous structure of said porous assembly is communicated with at least one aperture and/or said channel of said adjoining porous structure.

2. The porous structure and the porous assembly as claimed in claim 1, wherein, said apertures are formed into geometric contours by said walls.

3. The porous structure and the porous assembly as claimed in claim 1, wherein, said aperture has a taper-shaped cross section.

4. The porous structure and the porous assembly as claimed in claim 1, wherein, a first width of an upper part of said aperture is smaller than a second width of a lower part of said aperture.

5. The porous structure and the porous assembly as claimed in claim 1, wherein, an arrangement of said aperture allows said porous structure to provide a boundary with indentations.

6. The porous structure and the porous assembly as claimed in claim 1, wherein, said channel is parallel to a horizontal reference axis.

7. The porous structure and the porous assembly as claimed in claim 1, wherein, said channel is disposed on a horizontal reference axis.

8. The porous structure and the porous assembly as claimed in claim 1, wherein, said channel is disposed on said walls.

9. The porous structure and the porous assembly as claimed in claim 1, wherein, said channel is disposed at a lower part of said wall.

10. The porous structure and the porous assembly as claimed in claim 1, wherein, said porous assembly is formed into a geometric contour.

11. The porous structure and the porous assembly as claimed in claim 1, wherein, said porous assembly is formed into a cylinder.

12. The porous structure and the porous assembly as claimed in claim 1, wherein, said porous structure is arranged on an object.

13. The porous structure and the porous assembly as claimed in claim 1, wherein, said channel of said porous structure is disposed between said first surface and said second surface.

14. The porous structure and the porous assembly as claimed in claim 1, wherein, said apertures are formed into regular and/or irregular geometric contours.

15. The porous structure and the porous assembly as claimed in claim 1, wherein, said apertures are arranged on said porous structure in a regular pattern and/or in an irregular pattern.

16. The porous structure and the porous assembly as claimed in claim 1, wherein, said porous structure is arranged on a surface of a fixing structure.

17. The porous structure and the porous assembly as claimed in claim 1, wherein, said porous structure adopts a flexible material for being formed into a sheet with a geometric contour.

18. The porous structure and the porous assembly as claimed in claim 1, wherein, said porous structure adopts a rigid material for being formed into a sheet with a geometric contour.

19. The porous structure and the porous assembly as claimed in claim 1, wherein, said porous structure is formed into a square contour.

20. The porous structure and the porous assembly as claimed in claim 1, wherein, said first surface is formed into a plane.

21. The porous structure and the porous assembly as claimed in claim 1, wherein, said second surface is formed into a plane.

* * * * *